(12) United States Patent
Terada et al.

(10) Patent No.: US 8,053,467 B2
(45) Date of Patent: Nov. 8, 2011

(54) FLAVOR IMPROVING AGENT, AND FOOD AND DRINK CONTAINING THE SAME

(75) Inventors: Ikuo Terada, Kanagawa (JP); Toshihiro Takeda, Kanagawa (JP); Tsuyoshi Kobayashi, Kanagawa (JP); Tadahiro Hiramoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 410 days.

(21) Appl. No.: 12/311,568

(22) PCT Filed: Oct. 5, 2007

(86) PCT No.: PCT/JP2007/070028
§ 371 (c)(1),
(2), (4) Date: Apr. 3, 2009

(87) PCT Pub. No.: WO2008/044784
PCT Pub. Date: Apr. 17, 2008

(65) Prior Publication Data
US 2010/0029786 A1   Feb. 4, 2010

(30) Foreign Application Priority Data
Oct. 6, 2006   (JP) ................... 2006-275847

(51) Int. Cl.
| C07D 307/02 | (2006.01) |
| C07D 315/00 | (2006.01) |
| C07D 407/00 | (2006.01) |
| A01N 25/00 | (2006.01) |
| A01N 43/08 | (2006.01) |
| A61K 47/00 | (2006.01) |
| A61K 31/34 | (2006.01) |
| A61K 8/18 | (2006.01) |
| A61Q 13/00 | (2006.01) |

(52) U.S. Cl. ........ 514/461; 514/772; 549/472; 426/536; 512/11
(58) Field of Classification Search .......... 514/461, 514/772; 549/472; 426/536
See application file for complete search history.

(56) References Cited

U.S. PATENT DOCUMENTS
| 3,584,013 A | 6/1971 | Buechi et al. |
| 4,179,526 A | 12/1979 | Withycombe et al. |
| 2006/0128844 A1 | 6/2006 | Sanborn et al. |

FOREIGN PATENT DOCUMENTS
| CH | 478 227 A | 9/1969 |
| JP | 09-313129 A | 12/1997 |
| JP | 10-265468 A | 10/1998 |
| JP | 11-318379 A | 11/1999 |
| JP | 2001-299264 A | 10/2001 |
| JP | 2005-506984 A | 3/2005 |
| WO | WO 03/024947 AL | 3/2003 |

OTHER PUBLICATIONS

Supplemental European Search Report dated Jan. 4, 2011, in corresponding EP 07829763.7, 4 pages.
International Search Report dated Nov. 20, 2007, in PCT/JP2007/070028, 3 pages.
Ito et al., "Aroma components of heated liquid sugar," Nippon Shokuhin Kogyo Gakkaishi, 1978, 25(10):549-555.

Primary Examiner — Sreeni Padmanabhan
Assistant Examiner — Kendra D Carter
(74) Attorney, Agent, or Firm — Foley & Lardner LLP

(57) ABSTRACT

The present invention provides a novel flavor improving agent capable of sufficiently enhancing or alleviating the flavor sensed in oral cavity; for example, enhancing and improving the thickness in taste or the like to provide depth and profoundness to the flavor, and also improving the sense of volume or the sharpness of aftertaste. The present invention also provides a food/drink, a pharmaceutical product and an oral care product having a good taste which can fulfill the recent high-level demand for taste.

16 Claims, No Drawings

FLAVOR IMPROVING AGENT, AND FOOD AND DRINK CONTAINING THE SAME

CROSS-REFERENCE TO RELATED APPLICATIONS

This application is a National Stage application of PCT/JP2007/070028, filed Oct. 5, 2007, which claims priority from Japanese application JP 2006-275847, filed Oct. 6, 2006.

TECHNICAL FIELD

The present invention relates to a novel compound having a flavor improving capability, a composition including the same, and a flavor improving agent including the same. The present invention also relates to an aroma material composition including a novel compound having a flavor improving capability and an aroma material. The present invention further relates to a food/drink, a pharmaceutical product, an oral care product and the like including either the flavor improving agent or the aroma material composition.

BACKGROUND ART

Because of the recent increase in health consciousness, sugar-free and low- or non-calorie foods and drinks are desired. These foods and drinks have health benefits such as promotion of dieting, prevention of obesity, prevention of tooth decay and the like, but still need to have some sweetness in order to taste good. Substances known as providing sweetness include sugar alcohols and high-intensity sweeteners (also referred to as "artificial sweeteners"), which are described in many study reports. The sugar alcohols and high-intensity sweeteners are often used for the above-mentioned foods and drinks as substitutes of sugar in order to increase the sweetness, but are reputed to have disadvantages that sugar does not have. For example, the sugar alcohols and high-intensity sweeteners do not provide depth or thickness in taste and have heavy aftertaste and astringency.

Conventionally, foods and drinks are devised in many ways to taste better. One such way is to put additives. Additives which are, for example, effective to provide thickness in taste and alleviate aftertaste and astringency have been reported. For example, hesperidin glycoside (patent document 1: Japanese Laid-Open Patent Publication No. 11-318379) and theanine, which is an ingredient of tea (patent document 2: Japanese Laid-Open Patent Publication No. 9-313129), have been reported as additives which provide a satisfactory flavor to foods or drinks.

The former flavor improving agent has an effect of reducing the heavy aftertaste but does not sufficiently alleviate the astringency and does not sufficiently provide depth or thickness in taste. Thus, the improving effect thereof is not satisfactory. The latter flavor improving agent is applicable to a wide range of foods and drinks but does not have a sufficient flavor improving effect.

DISCLOSURE OF THE INVENTION

With such a background, a novel flavor improving agent capable of sufficiently improving or enhancing the flavor sensed in oral cavity by, for example, improving the sharpness of aftertaste, reducing the astringency and improving the sense of volume, and thus capable of improving the attractiveness of foods, drinks and the like is desired. Also desired is a novel flavor improving agent which enhances or improves the sense of roastedness, the sense of naturalness, the sense of refreshment, thickness in taste or the like to provide depth and profoundness to the taste, and thus is capable of improving the flavor with even a small amount. Further desired is a novel flavor improving agent which reduces the disadvantages of sugar alcohols and high-intensity sweeteners, such as heavy aftertaste, astringency and lack in the sense of volume to provide sharp aftertaste and provides thickness in taste and the so-called sense of volume to drinks and foods.

While studying in various ways in order to solve the above-described problems, the present inventors found that a specific acetal compound, when being added to drinks containing sugar alcohols or high-intensity sweeteners, surprisingly solves the problems thereof and provides drinks with a significantly better flavor. The present inventors also found that the acetal compound has a flavor improving effect for a wide range of foods and drinks of, for example, adding bitterness, or enhancing or improving the sense of roastedness, the sense of naturalness, the sense of refreshment, thickness in taste or the like to provide depth and profoundness to the flavor, depending on the amount added. The present inventors determined the structure of the acetal compound, and found that the compound has not been described yet in any literature. Based on such study achievements, the present inventors accumulated further studies and completed the present invention.

The present invention relates to a compound; a composition, a flavor improving agent, and an aroma material composition including the compound; and a food/drink, a pharmaceutical product, an oral care product and the like including them.

[1] 5-hydroxymethyl-2-furaldehyde bis(5-formylfurfuryl) acetal.

[2] A composition comprising at least 0.1% by weight of 5-hydroxymethyl-2-furaldehyde bis(5-formylfurfuryl) acetal.

[3] A composition comprising at least 0.7% by weight of 5-hydroxymethyl-2-furaldehyde bis(5-formylfurfuryl) acetal.

[4] A flavor improving agent comprising 5-hydroxymethyl-2-furaldehyde bis(5-formylfurfuryl)acetal as an effective ingredient.

[5] The flavor improving agent according to [4], further comprising an aroma material.

[6] The flavor improving agent according to [4] or [5], wherein the content of 5-hydroxymethyl-2-furaldehyde bis(5-formylfurfuryl)acetal is at least 0.1% by weight.

[7] The flavor improving agent according to [4] or [5], wherein the content of 5-hydroxymethyl-2-furaldehyde bis(5-formylfurfuryl)acetal is at least 0.7% by weight.

[8] An aroma material composition comprising 5-hydroxymethyl-2-furaldehyde bis(5-formylfurfuryl)acetal and an aroma material.

[9] The aroma material composition according to [8], wherein the content of 5-hydroxymethyl-2-furaldehyde bis(5-formylfurfuryl)acetal is 0.000001 to 50% by weight.

[10] The aroma material composition according to [8], wherein the content of 5-hydroxymethyl-2-furaldehyde bis(5-formylfurfuryl)acetal is 0.00001 to 10% by weight.

[11] A food/drink comprising the flavor improving agent according to any one of [4] through [7] or the aroma material composition according to any one of [8] through [10].

[12] The food/drink according to [11], wherein the content of 5-hydroxymethyl-2-furaldehyde bis(5-formylfurfuryl)acetal is 1 ppb to 1000 ppm.

[13] A pharmaceutical product comprising the flavor improving agent according to any one of [4] through [7] or the aroma material composition according to any one of [8] through [10].

[14] The pharmaceutical product according to [13], wherein the content of 5-hydroxymethyl-2-furaldehyde bis(5-formylfurfuryl)acetal is 1 ppb to 1000 ppm.

[15] An oral care product comprising the flavor improving agent according to any one of [4] through [7] or the aroma material composition according to any one of [8] through [10].

[16] The oral care product according to [15], wherein the content of 5-hydroxymethyl-2-furaldehyde bis(5-formylfurfuryl)acetal is 1 ppb to 1000 ppm.

Herein, the term "flavor improving agent" refers to an agent having an effect of reducing or alleviating undesirable flavor or displeasing sensation or enhancing desirable flavor to improve the attractiveness, and thus improving the original taste and aroma to a better taste and aroma. The term "aroma material composition" refers to a compound adding aroma.

The present invention provides a flavor improving agent capable of improving the flavor of foods/drinks, pharmaceutical products, oral care products and the like. According to a preferable embodiment of the present invention, the flavor improving agent, when being incorporated into foods/drinks, can improve the sharpness of aftertaste and the sense of volume, provide the sense of roastedness, the sense of naturalness, the sense of refreshment, thickness in taste and the like, and also remove the astringency and heaviness of aftertaste of the foods/drinks. When the flavor improving agent of the present invention is incorporated, highly attractive foods/drinks can be provided. The flavor improving agent provides a very practical effect of allowing the flavor of foods/drinks to be sensed more in oral cavity so that the foods/drinks are tasted delicious.

The flavor improving agent of the present invention, when being incorporated into pharmaceutical products, can reduce the difficulty in taking the pharmaceutical products. When the flavor improving agent of the present invention is incorporated into oral care products, the oral care products can have an improved flavor.

The present invention also provides an aroma material composition capable of adding a desired aroma to foods/drinks, pharmaceutical products, oral care products and the like and also capable of improving the flavor thereof.

BEST MODE FOR CARRYING OUT THE INVENTION

Hereinafter, the present invention will be described in detail.

1. 5-hydroxymethyl-2-furaldehyde bis(5-formylfurfuryl) acetal

First, 5-hydroxymethyl-2-furaldehyde bis(5-formylfurfuryl)acetal will be described.

5-hydroxymethyl-2-furaldehyde bis(5-formylfurfuryl)acetal, which has been found by the present inventors for the first time in history, is expressed by the formula:

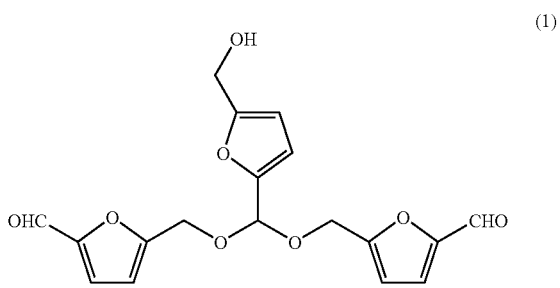

and is a colorless or pale yellow oily substance (hereinafter, this substance will also be referred to as the "acetal compound of the present invention"). The acetal compound of the present invention is bitter or enriched in taste, and has an effect of improving the flavor of foods/drinks, pharmaceutical products, oral care products or the like, when being added thereto. According to a preferable embodiment of the present invention, the acetal compound of the present invention, when being added to foods/drinks or the like, can improve the sharpness of aftertaste and the sense of volume and can also provide the sense of roastedness, the sense of naturalness, the sense of refreshment, thickness in taste or the like. The acetal compound of the present invention also has an effect of reducing unpleasant aftertaste or astringency.

As described in more detail later in a reference example, the bitterness threshold of the acetal compound of the present invention was evaluated as 1 ppm (0.0001%) by a sensory evaluation test. By contrast, the compounds expressed by formulas (2) and (3):

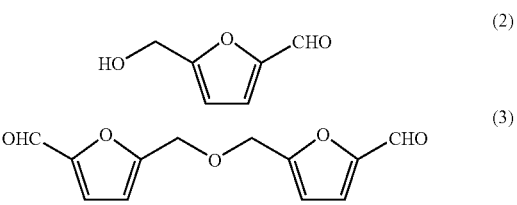

which are similar substances to the acetal compound of the present invention, did not provide bitterness even at a concentration 1000 times higher (0.1%). The compounds expressed by formulas (2) and (3) both have been reported to have an unpleasant taste (Journal of Food Science and Technology, Vol. 27, No. 7, 1980). From these, it can be understood that the bitter or enriched taste provided by the acetal of the present invention and the flavor improving effect provided by such a taste are specific to the acetal compound of the present invention and is not expectable from the structure thereof.

The acetal compound of the present invention can be synthesized by stirring 5-hydroxymethyl-2-furaldehyde shown by formula (2) in the presence of an acid catalyst. 5-hydroxymethyl-2-furaldehyde is a known compound and is commercially available from Tokyo Chemical Industry Co., Ltd. As the acid catalyst, strong acid cation exchange resin for non-water, sulfuric acid, hydrochloric acid or the like is usable. The reaction is preferably performed under a low temperature condition of, for example, about 0 to 20° C. The reaction is also preferably performed along with dewatering with a dehydrating agent. After the reaction, the intended compound can be obtained by conducting separation and refinement in accordance with a conventional method. A specific synthesis method is described in Example 1. The acetal compound of the present invention can also be obtained by isolation from a composition of the present invention prepared by a method described later.

2. Composition containing 5-hydroxymethyl-2-furaldehyde bis(5-formylfurfuryl)acetal A composition of the present invention contains at least 0.1% by weight of the acetal compound of the present invention. The composition of the present invention, which contains at least 0.1% by weight of the acetal compound of the present invention, can provide a flavor improving effect with a small amount. Therefore, when added to foods/drinks and the like, the composition of the present invention can minimize the influence of calorie increase or the like and the problems of coloring and addition of other tastes due to contamination with impurities. For these reasons, the composition of the present invention is useful as a flavor improving agent. When the content of the acetal compound of the present invention in the composition is less than 0.1% by weight, the composition cannot provide the flavor improving effect with a small amount. It is not preferable to add the composition in an excessive amount either because the problems of calorie increase, coloring and the like arise. The content of the acetal compound in the composition of the present invention is preferably at least 0.10% by weight, more preferably at least 0.7% by weight, still more preferably at least 1% by weight, especially preferably at least 5% by weight, and most preferably at least 10% by weight.

The flavor improving agent of the present invention can reduce or alleviate undesirable flavor or displeasing sensation, or can enhance desirable flavor, to improve the attractiveness. Examples of the desirable flavor, undesirable flavor and displeasing sensation include, but not limited to, sour taste, thickness in taste, bitter taste, salty taste, sweet taste, umami, harsh taste, astringency, hot taste, aroma, sense of volume, texture, sense of refreshment, sharpness of bitter taste and heavy aftertaste and the like.

The composition of the present invention may further contain a carrier of the acetal compound of the present invention. Herein, the term "carrier" refers to a substance usually used for adding or incorporating the acetal compound of the present invention to any other substance or product. Specific examples of the carrier include liquid carriers and solid carriers. Examples of the liquid carriers include water, ethanol, water-containing ethanol, propyleneglycol, glycerin, triacetin, benzyl alcohol, triethyl citrate, fats and oils and the like. Examples of the solid carriers include polysaccharides, processed starch and the like. According to the present invention, known emulsifiers, dispersants, suspending agents and the like are also usable as the carriers.

The composition of the present invention can be obtained by extraction with a solvent from a substance which is obtained by heating a mixture solution containing sugar and water at 80 to 220° C. under an acid condition.

Examples of the usable sugar include monosaccharides, disaccharides, and polysaccharides including trisaccharides. Examples of the monosaccharides include fructose, glucose, galactose, mannose and the like. Examples of the disaccharides include sucrose, lactose, maltose and the like. Examples of the polysaccharides include cellulose and starch. As the sugar, mixtures such as hydrolyzed starch, molasses, caramel and the like are also usable. Among these sugars, fructose, glucose and sucrose are preferable, and fructose is especially preferable. These sugars may be used independently or as a combination of two or more.

The sugar is preferably heated together with an appropriate amount of water. Without water, it is difficult to heat the sugar uniformly. It is not economical to use an excessive amount of water because the heating time is extended. The amount of water also varies in accordance with the heating method and the like. For example, when the heating is performed in the form of refluxing, the amount of water is preferably 100 to 300% by weight, based on the weight of the sugar. When the heating is performed in an open system using an oven or the like, the amount of water is preferably 10 to 50% by weight, based on the weight of the sugar.

According to the present invention, the heating is performed under an acid condition. The acid may be a strong acid or a weak acid. When the heating is performed in the form of refluxing, a strong acid is preferable. Examples of the strong acid include sulfuric acid, hydrochloric acid, and strong acid ion exchange resin. When the heating is performed in an open system using an oven or the like, a weak acid is preferable. Examples of the weak acid include acetic acid, lactic acid, citric acid, and phosphoric acid. When the heating is performed in the form of refluxing, the acid is used in such an amount that the pH value of the mixture solution is preferably about 1 to 5, more preferably about 1 to 3, and still more preferably about 1 to 2. When the heating is performed in an open system using an oven or the like, the acid is used in such an amount that the pH value of the mixture solution is preferably about 1 to 5, more preferably about 1 to 3, and still more preferably about 2 to 3.

The heating temperature is preferably 80 to 220° C.

The heating is performed until the heated substance becomes brown or dark brown. The heating time significantly varies in accordance with the heating temperature, the amount of the substance to be heated, the amount of water, the pressure, the heating power and the like, and cannot be precisely specified easily. For example, when the heating is performed in the form of refluxing at 100° C., the heating time is preferably about 3 to 8 hours. When the heating is performed in an open system using an oven or the like, the heating time is preferably about 1 to 8 hours at a heating temperature in the range of 100 to 150° C., and is preferably about 5 hours at a heating temperature of 120° C.

After the heating, the composition of the present invention can be obtained by extraction with a solvent from the substance obtained by the heating. When the heating is performed in an open system using an oven or the like, the extraction with a solvent is performed after the substance obtained by the heating is diluted with water.

There is no specific limitation on the solvent used for the extraction as long as the acetal compound of the present invention is extracted. Specific examples of the solvent usable for the extraction include lower alcohols such as methanol, ethanol, propanol, isopropanol and the like; polyhydric alcohols such as 1,3-butyleneglycol, propyleneglycol, dipropyleneglycol, glycerin and the like; ethers such as ethylether, propylether and the like; esters such as ethyl acetate, butyl acetate and the like; ketones such as acetone, ethylmethylketone and the like; hydrocarbons such as n-hexane, benzene and the like; and halogen solvents such as chloroform, methylene chloride and the like. These solvents may be used independently or as a combination of two or more. Among these solvents, ethylether and ethyl acetate are preferable. There is no specific limitation on the amount of the solvent for the extraction. For example, it is practical to use the solvent in the range of the equivalent amount to 10 times (by weight) the amount of the sugar as the raw material.

The resultant extract solution is washed with water, and the moisture component is removed with magnesium sulfate anhydride or the like. Then, the resultant substance is concentrated under reduced pressure to a desired concentration to provide the composition of the present invention. When necessary, the carrier described above may be added to the composition to process the composition into a desired form.

According to a preferable embodiment of the present invention, the composition of the present invention can be obtained by heating a mixture solution containing sugar and water to be refluxed at about 100° C. for about 3 to 8 hours in an acid condition of a pH value of 1 to 5, preferably 1 to 3, and more preferably 1 to 2, which is realized by addition of an acid; then performing extraction from the resultant heated substance with ethyl acetate; and concentrating the extracted substance to a desired concentration. Alternatively, the composition of the present invention can be obtained by heating a mixture solution containing sugar and water in an open system at about 100° C. to 150° C. for about 1 to 8 hours in an acid condition of a pH value of 1 to 5, preferably 1 to 3, and more preferably 2 to 3, which is realized by addition of an acid; then performing extraction from the resultant heated substance with ethyl acetate; and concentrating the extracted substance to a desired concentration.

Isolation of the acetal compound of the present invention from the obtained composition can be performed using ordinary refining means such as column chromatography or the like.

The composition of the present invention obtained in this manner is preferably usable as a flavor improving agent contained in foods/drinks, pharmaceutical products, oral care products and the like.

3. Flavor Improving Agent

A flavor improving agent of the present invention contains the acetal compound of the present invention as an effective ingredient and therefore can improve the flavor and attractiveness of foods/drinks, pharmaceutical products, oral care products and the like when being contained therein.

There is no specific limitation on the content of the acetal compound in the flavor improving agent of the present invention, but the content is preferably at least 0.1% by weight, more preferably at least 0.7% by weight, especially preferably at least 1% by weight, still more preferably at least 5% by weight, and most preferably at least 10% by weight. When the content of the acetal compound is at least 0.1% by weight, the flavor improving agent has a high flavor improving effect and can provide a desired effect with a small amount.

The flavor improving agent of the present invention may further contain a carrier of the acetal compound of the present invention. Examples of the carrier usable for the flavor improving agent of the present invention are the same as those mentioned above regarding the composition of the present invention. From these substances, an appropriate carrier may be selected based on the usage or form of the flavor improving agent.

The flavor improving agent of the present invention may further contain an aroma material in order to improve the aroma note.

As an aroma material, any of aroma materials such as natural aroma materials, natural essential oils and the like; and various types of synthetic aroma materials usable for foods/drinks can be used. Examples of preferable aroma materials include synthetic aroma materials such as esters, alcohols, aldehydes, ketones, acetals, phenols, ethers, lactones, furans, hydrocarbons, acids and the like; essential oils of citrus fruits such as orange, lemon, lime, grapefruit and the like; essential oils prepared from flowers; essential oils of plants such as peppermints, spearmints, spice oils and the like; oily extracts such as kolanut extract, coffee extract, vanilla extract, cocoa extract, black tea extract, green tea extract, oolong tea extract, spice extract and the like, and oleoresins thereof; natural aroma materials such as essences, recovered aroma materials and the like; and mixtures of a plurality of aroma materials and essential oils selected from these. Also usable are aroma materials described in "Research on Use of Aroma Material Compound for Food in Japan" (Report of health science studies in 2000, Japan Flavor and Fragrance Materials Association, issued in March 2001), "Synthetic Aroma Materials: Chemistry and Knowledge on Products" (Motoichi INDO, issued on Mar. 6, 1996, The Chemical Daily Co., Ltd.), "Perfume and Flavor Chemicals (Aroma Chemicals) 1, 2" (Steffen Arctender, 1969), and the like.

In the flavor improving agent of the present invention, the amount of the aroma material significantly varies in accordance with the food/drink to which the flavor improving agent is to be added, the aroma material to be used and the like, and cannot be specified easily. Even a very small amount may be effective, or a very large amount is occasionally used. The amount is not specifically limited.

With the flavor improving agent of the present invention, other additives may be mixed as long as the object of the present invention is achieved. Any additive which does not completely inhibit the effect of the flavor improving agent of the present invention is usable with no specific limitation. Additives usually used for foods/drinks, pharmaceutical products and oral care products are usable.

Specific examples of such additives include acidulant, extender, antioxidant, pigment, known preservative or antibacterial agent, functional substance, existent flavor improving agent, pH adjuster, milk component and nitrogen-containing compound such as amino acid or peptide. These additives may be used independently or as a combination of two or more. There is no specific limitation on the amount of such an additive as long as the object of the present invention is achieved.

Examples of the acidulant include acetic acid, lactic acid and citric acid. Examples of the extender include sugars, polysaccharides, processed starch, casein, gelatin, carboxymethylcellulose, lecithin and the like.

Known examples of the antioxidant include butylhydroxytoluene, butylhydroxyanisol, citric acid, bioflavo acid, glutathione, selenium, lycopene, vitamin A, vitamin E, vitamin C, etc., and also free radical scavengers obtained from the extract from pyrrolopyrrole derivatives or various types of plants, and enzymes having an antioxidant property such as superoxide dismutase and glutathioneperoxidase.

Known examples of the pigment include natural pigments and organic synthetic pigments which are not hazardous to humans. Specific examples of the pigments include hibiscus pigment, huckleberry pigment, plum pigment, seaweed pigment, dewberry pigment, grape juice pigment, blackberry pigment, blueberry pigment, mulberry pigment, morello cherry pigment, red currant pigment, loganberry pigment, paprika powder, malt extract, rutin, flavonoid, red cabbage pigment, red radish pigment, adzuki bean pigment, turmeric pigment, olive tea, cowberry pigment, chlorella powder, saffron pigment, perilla pigment, strawberry pigment, chiocory pigment, pecan nut pigment, ang-khak pigment, safflower pigment, purple sweet potato pigment, lac pigment, spirlina pigment, onion pigment, tamarind pigment, red pepper pigment, Cape jasmine pigment, caramel pigment, lithospermum root pigment, rosewood pigment, krill pigment, orange pigment, and carrot carotin.

Examples of the known preservative and antibacterial agent include benzoic acid, sodium benzoate, isopropyl p-hydroxybenzoate, isobutyl p-hydroxybenzoate, ethyl p-hydroxybenzoate, methyl p-hydroxybenzoate, butyl p-hydroxybenzoate, propyl p-hydroxybenzoate, sodium sulfite, sodium hyposulfite, potassium pyrosulfite, sorbic acid, potassium sorbate, sodium dehydroacetate, thujaplicin, udo extract, Japanese snowbell extract, *Artemisia capillaris* extract, oolong tea extract, soft roe protein extract, enzyme-decomposed *Coix lacryma-jobi* L. var. *ma-yuen* extract, tea catechins, apple polyphenol, pectin-decomposed substance, chitosan, lysozyme, ϵ-polylysine and the like.

The "functional substance" means a substance having a nutritious function or a living body adjusting function. Examples of the functional substance include animal and plant fats and oils such as docosahexaenoic acid (DHA), eicosapentaenoic acid (EPA), DHA- and/or EPA-containing fish oil, linoleic acid, γ-linolenic acid, α-linolenic acid, lecithin, diacylglycerol and the like, and derivatives thereof; animal and plant extracts such as rosemary, sage, perilla oil, chitin, chitosan, royal jelly, propolis and the like; vitamins, coenzymes and derivatives such as vitamin A, vitamin D, vitamin E, vitamin F, vitamin K, coenzyme Q10, α-lipoic acid and the like; polyphenols such as γ-oryzanol, catechin, anthocyanin, isoflavone, rutin, chlorogenic acid, theaflavin and the like; vegetable fibers such as hard-to-digest dextrin and the like; sugars such as palatinose, xylitol, oligosaccharide and the like; salts such as calcium citrate malate and the like; lactoprotein-derived substances such as casein phosphopeptide, lactoferrin, lactic peptide and the like; lactic bacteria; γ-aminobutyric acid; heme iron and the like.

The "pH adjuster" means a substance or a formulation usable for keeping the pH value of the food within an appropriate range. Examples of the pH adjuster include adipic acid, citric acid, trisodium citrate, glucono-δ-lactone, gluconic acid, potassium gluconate, sodium gluconate, succinic acid, monosodium succinate, disodium succinate, sodium acetate, DL-tartaric acid, L-tartaric acid, DL-potassium hydrogen tartrate, L-potassium hydrogen tartrate, DL-sodium tartrate, L-sodium tartrate, potassium carbonate (anhydride), sodium hydrogen carbonate, sodium carbonate, carbon dioxide, lactic acid, sodium lactate, glacial acetic acid, disodium dihydrogen pyrophosphate, fumaric acid, monosodium fumarate, DL-malic acid, DL-sodium malate, phosphoric acid, dipotassium hydrogen phosphate, potassium dihydrogen phosphate, disodium hydrogen phosphate, sodium dihydrogen phosphate, and other acidulants.

Examples of the milk component include raw milk; milk; milk powder; skimmed milk powder; fresh cream, etc.; and also lactoprotein such as casein, whey and the like; substances derived from, for example, goat milk or sheep milk; and substances obtained by decomposing these substances.

With the flavor improving agent of the present invention, a known flavor improving agent such as sucralose, cyclodextrin, theanine, hesperidin glycoside, sugar cane extract or the like may be mixed.

The flavor improving agent of the present invention is prepared by adding, optionally, an aroma material and an additive to the acetal compound of the present invention. The flavor improving agent of the present invention may also be prepared using the composition of the present invention described above instead of the acetal compound of the present invention.

The flavor improving agent of the present invention is usable for various foods/drinks as it is, or in the form of a diluted solution using a solvent such as ethanol or the like. The flavor improving agent of the present invention may be used after being processed into powder, granule or the like with any of various coating agents. The flavor improving agent of the present invention may be processed into powder, granule or the like by mixing the flavor improving agent with a generally used coating agent and processing the mixture by, for example, spray drying or freeze drying. Examples of the coating agent include gum Arabic, pullulan, tragacanth gum, cyclodextrin, dextrin, gelatin, processed starch and the like. The flavor improving agent of the present invention is also usable in any other form, for example, paste or emulsion. The flavor improving agent of the present invention is usable in a mixture with any of various additives or any of various known flavoring materials, or may be mixed with any other appropriate prepared aroma material composition for foods.

4. Aroma Material Composition

Now, an aroma material composition of the present invention will be described.

The aroma material composition of the present invention contains the acetal compound of the present invention and an aroma material. The aroma material composition of the present invention contains the acetal compound of the present invention having a flavor improving effect together with an aroma material, and has an effect of providing a desired aroma to foods/drinks or the like as well as an effect of improving the flavor of foods/drinks.

In the aroma material composition of the present invention, there is no specific limitation on the amount of the acetal compound of the present invention. Since the acetal compound of the present invention provides a desired flavor improving effect with a small amount, the amount of the acetal compound is preferably 0.000001 to 50% by weight, more preferably 0.00001 to 10% by weight, and still more preferably 0.0001 to 5% by weight.

As the aroma material in the aroma material composition of the present invention, aroma materials such as natural aroma materials, natural essential oils and the like; and various synthetic aroma materials usable for foods/drinks can be used. Specific examples of the aroma materials are the same as those mentioned above as optional components of the flavor improving agent of the present invention.

The aroma material composition of the present invention may optionally contain a carrier and an additive when necessary in addition to the above-mentioned substances. Specific examples of the carrier and the additive, the amounts thereof, and the methods for preparing the aroma material composition are the same as described above regarding the flavor improving agent of the present invention.

5. Foods/Drinks, Pharmaceutical Products and Oral Care Products (1) Foods/Drinks The flavor improving agent or aroma material composition prepared in this manner can improve the flavor of foods/drinks when being incorporated thereto.

There is no specific limitation on the foods/drinks to which the flavor improving agent can be incorporated. Examples of such foods/drinks include processed foods based on meat, poultry meat, fish/shellfish and the like; soup; seasonings including sweetener and the like; rice seasonings; instant foods; frozen foods; snacks; various types of functional foods such as supplements, nutritional drinks and the like; canned foods; dairy products; confectionery such as chewing gum, candy, gummy candy, chocolate, baked sweets and the like; ice cream; soft drinks such as tea, coffee, cocoa, fruit juice, sports drink, carbonated drink, vegetable drink and the like; liquors; soya milk; lactic acid bacteria beverages; and chlorophyll juice. There is no specific limitation on the type of sweetener described above. Examples of the sweetener include sucrose, fructose, lactose, glucose, palatinose, malt sugar, trehalose, sorbitol, erythritol, maltitol, reduced palatinose, xylitol, lactitol, thick malt syrup, oligosaccharide, aspartame, sucralose, acesulfame K, saccharine, stevia, neotame, alitame, thaumatin, neohesperidinedihydrochalcone and licorice; and also sugar-free foods/drinks, non-calorie foods/drinks, and low-calorie foods/drinks using the above-listed sweeteners. The amount of the flavor improving agent or aroma material composition of the present invention varies in accordance with the type of the flavor improving agent or aroma material composition, the type of food/drink, the method of applying the flavor improving agent or aroma material composition, the method of use and the like. For example, the flavor improving agent or aroma material composition of the present invention is generally used in an amount of about 0.000001 to 20% by weight, and more preferably in an amount of about 0.00001 to 10% by weight, with respect to the food/drink. The content of the acetal compound of the present invention in a food/drink is preferably 1 ppb to 1000 ppm, more preferably 5 ppb to 500 ppm, and still more preferably 10 ppb to 100 ppm.

(2) Pharmaceutical Products

The flavor improving agent or aroma material composition prepared as described above can be incorporated into pharmaceutical products and improve the flavor thereof. The "pharmaceutical products" in the present invention refers to pharmaceutical products and quasi-drugs defined in the Pharmaceutical Affairs Law.

There is no specific limitation on the pharmaceutical products into which the flavor improving agent or aroma material composition can be incorporated. Examples of the pharmaceutical products include liquid, granular, and powdery internal medicine. The amount of the flavor improving agent or aroma material composition of the present invention varies in accordance with the type of the flavor improving agent or aroma material composition, the type of pharmaceutical product, the method of applying the flavor improving agent or aroma material composition, the method of use and the like. For example, the flavor improving agent or aroma material composition of the present invention is generally used in an amount of about 0.000001 to 20% by weight, and more preferably in an amount of about 0.00001 to 10% by weight, with respect to the pharmaceutical product. The content of the acetal compound of the present invention in a pharmaceutical product is preferably 1 ppb to 1000 ppm, more preferably 5 ppb to 500 ppm, and still more preferably 10 ppb to 100 ppm.

(3) Oral Care Products

The flavor improving agent or aroma material composition prepared as described above can be incorporated into oral care products and improve the flavor thereof.

There is no specific limitation on the oral care products into which the flavor improving agent or aroma material composition can be incorporated. Specific examples of the oral care products include various types of mouse washes, various types of dentifrices, chewing gum for oral care, and other oral care products in the forms of candy, tablet, capsule, mouth spray, and film. The amount of the flavor improving agent or aroma material composition of the present invention varies in accordance with the type of the flavor improving agent or aroma material composition, the type of the oral care product, the method of applying the flavor improving agent or aroma material composition, the method of use and the like. For example, the flavor improving agent or aroma material composition of the present invention is generally used in an amount of about 0.000001 to 20% by weight, and more preferably in an amount of about 0.00001 to 10% by weight, with respect to the oral care product. The content of the acetal compound of the present invention in an oral care product is preferably 1 ppb to 1000 ppm, more preferably 5 ppb to 500 ppm, and still more preferably 10 ppb to 100 ppm.

The flavor improving agent of the present invention is effective to improve a wide range of flavors, and can improve the flavor such as, for example, astringency, bitter taste, sharpness of bitter taste, aftertaste, heaviness of aftertaste and the like.

EXAMPLES

Hereinafter, the present invention will be described more specifically with reference to examples. It should be noted that the present invention is not limited to these examples.

Example 1

Preparation of 5-hydroxymethyl-2-furaldehyde bis(5-formylfurfuryl)acetal 2.02 g (16.0 mmol) of 5-hydroxymethyl-2-furaldehyde was dissolved in 100 mL of ethyl acetate, and 200 mg of strong acid cation exchange resin for non-water as an acid catalyst and a small amount of molecular sieve as a dehydrating agent were added thereto. These substances were stirred to react at 4° C. for 3 days, and then the acid catalyst and the molecular sieve were filtered out by a paper filter and stop the reaction. The obtained substance was concentrated under reduced pressure using an evaporator to obtain 1.98 g of a crude reaction product. The crude reaction product was subjected to silica gel column chromatography (hexane/ethyl acetate=1:2), and thus 47.1 mg of 5-hydroxymethyl-2-furaldehyde bis(5-formylfurfuryl)acetal (0.13 mmol, yield: 2.33% by weight) was obtained.

The spectral data of the obtained compound is as follows.
ESI-MS (m/z) [M+Na]+383.080-$^1$H NMR δ (CDCl$_3$): 9.53(2H, s) 7.13(2H, d, J=3.6 Hz) 6.46(2H, d, J=3.6 Hz) 6.40(1H, d, J=3.2 Hz) 6.21(1H, d, J=3.2 Hz) 5.71(1H, s) 4.60(4H, s) 4.52(2H, s)-$^{13}$C NMR δ (CDCl$_3$) 177.66, 157.32, 154.96, 152.75, 149.17, 122.11, 111.76, 110.49, 108.31, 95.81, 59.46, 57.34

The correlation of $^2J_{CH}$, $^3J_{CH}$ observed by the -HMBC (Heteronuclear Multiple-Bond Correlation) spectrum is represented by arrows as follows.

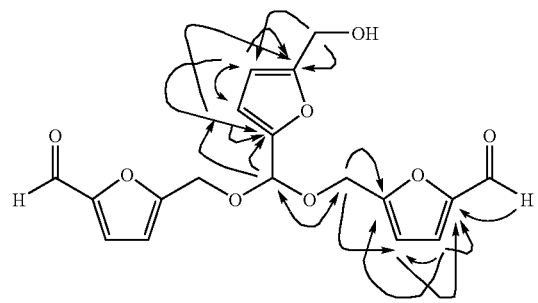

The devices used for the analysis were as follows.
MS measuring device: LCMS-IT-TOF (Shimadzu Corporation)
NMR measuring device: Instrument DRX500 (BRUKER BIOSPIN K.K)

Example 2

Preparation of a Flavor Improving Agent 1 g of ethanol was added to 7 mg of the compound obtained in Example 1 to prepare a flavor improving agent formed of a 0.7 wt. % ethanol solution of 5-hydroxymethyl-2-furaldehyde bis(5-formylfurfuryl)acetal.

Example 3

Preparation of a Flavor Improving Agent 1 g of ethanol was added to 300 mg of the crude reaction product in Example 1 to prepare a flavor improving agent formed of a 30 wt. % ethanol solution of the crude reaction product. The content of 5-hydroxymethyl-2-furaldehyde bis (5-formylfurfuryl)acetal was 0.7% by weight.

Example 4

Preparation of a Flavor Improving Agent

The crude reaction product in Example 1 was used as the flavor improving agent. The content of 5-hydroxymethyl-2-furaldehyde bis(5-formylfurfuryl)acetal was 2.33% by weight.

Example 5

Preparation of a Flavor Improving Agent 120 g of water was added to 46.8 g of sucrose, then 0.8 g of hydrochloric acid was added, and the resultant substance was heated to be refluxed at 100° C. for 4 hours. After the substance was cooled down, extraction with 120 mL of ethyl acetate was repeated 3 times, and the obtained extract solution was washed with 50 mL of water. An appropriate amount of magnesium sulfate anhydride was added to perform dehydrating overnight. Then, magnesium sulfate was filtered out by a paper filter, and the filtrate was concentrated under reduced pressure using an evaporator to obtain 3.15 g of a flavor improving agent. From this flavor improving agent, 5-hydroxymethyl-2-furaldehyde bis(5-formylfurfuryl)acetal was obtained at a yield of 4.6% by weight by substantially the same refining means as that in Example 1.

Example 6

Preparation of a Flavor Improving Agent 30 g of water was added to 100 g of fructose, then 1 g of citric acid was added, and the resultant substance was heated at 120° C. for 5 hours in an open system. After the substance was cooled down to such a degree that would not cause solidification, the resultant substance was dissolved in 200 mL of warm water. Extraction with 200 mL of ethyl acetate was repeated 3 times, and the obtained extract solution was washed with 30 mL of water. An appropriate amount of magnesium sulfate anhydride was added to perform dehydrating overnight. Then, magnesium sulfate was filtered out by a paper filter, and the filtrate was concentrated under reduced pressure using an evaporator to obtain 3.02 g of a flavor improving agent. From this flavor improving agent, 5-hydroxymethyl-2-furaldehyde bis(5-formylfurfuryl)acetal was obtained at a yield of 1.9% by weight by substantially the same refining means as that in Example 1.

Example 7

Preparation of a Flavor Improving Agent 55 mg of the flavor improving agent in Example 6 was dissolved in 1 mL of ethanol to prepare a flavor improving agent formed of a 5.5 wt. % ethanol solution of the flavor improving agent. The content of 5-hydroxymethyl-2-furaldehyde bis(5-formylfurfuryl)acetal was 0.10% by weight.

Comparative Example 1

Preparation of a Flavor Improving Agent 30 g of water was added to 100 g of fructose and heated at 120° C. for 5 hours in an open system. After the resultant substance was cooled down to such a degree that would not cause solidification, the resultant substance was dissolved in 200 mL of warm water. Extraction with 200 mL of ethyl acetate was repeated 3 times, and the obtained extract solution was washed with 30 mL of water. An appropriate amount of magnesium sulfate anhydride was added to perform dehydrating overnight. Then, magnesium sulfate was filtered out by a paper filter, and the filtrate was concentrated under reduced pressure using an evaporator to obtain 2.84 g of a flavor improving agent. The content of 5-hydroxymethyl-2-furaldehyde bis(5-formylfurfuryl)acetal in this flavor improving agent was 0.033% by weight.

Comparative Example 2

Preparation of a Flavor Improving Agent 30 g of water was added to 100 g of fructose, then 1 g of citric acid was added, and the resultant substance was heated at 120° C. for 5 hours in an open system. After the substance was cooled down to such a degree that would not cause solidification, the resultant substance was dissolved in 100 mL of warm water to obtain 170 g of a flavor improving agent. The content of 5-hydroxymethyl-2-furaldehyde bis(5-formylfurfuryl)acetal in this flavor improving agent was 0.017% by weight.

Comparative Example 3

Preparation of a Flavor Improving Agent 30 g of water was added to 100 g of fructose and heated at 120° C. for 5 hours in an open system. After the resultant substance was cooled down to such a degree that would not cause solidification, the resultant substance was dissolved in 100 mL of warm water to obtain 163 g of a flavor improving agent. From this flavor improving agent, 5-hydroxymethyl-2-furaldehyde bis(5-formylfurfuryl)acetal was not obtained.

Example 8

Preparation of an Aroma Material Composition 5-hydroxymethyl-2-furaldehyde bis(5-formylfurfuryl)acetal obtained in Example 1 was mixed with a aroma material and diluted with a solvent with the formulation shown in Table 1 to prepare an aroma material composition.

TABLE 1

| Formulation of the aroma material composition | |
|---|---|
| Acetal compound of the present invention | 0.7 g |
| Chocolate flavor | 20 g |
| Propyleneglycol | 79.3 g |
| Total | 100 g |

The chocolate flavor in the table is "E-25430" produced by Takasago International Corporation.

Example 9

Preparation of a Sugar-Free Sweetener Containing a Flavor Improving Agent

A sugar-free sweetener having the formulation shown in Table 2 was obtained, and 12 g of the sugar-free sweetener was dissolved in 1 kg of ion exchanged water to obtain a 1.2 wt. % aqueous solution. 60 mg of the flavor improving agent in Example 2 was added to 300 g of the aqueous solution to obtain a sugar-free sweetener solution sample containing 0.02% by weight of the flavor improving agent. The content of 5-hydroxymethyl-2-furaldehyde bis(5-formylfurfuryl)acetal in the sugar-free sweetener was 0.00014% by weight.

TABLE 2

| Formulation of the high-intensity sweetener model powder | |
| --- | --- |
| Aspartame | 0.8 |
| Acesulfame K | 0.32 |
| Maltitol | 73.88 |
| Erythritol | 20 |
| Food fiber (dextrin) | 5 |
| Total | 100 |

This sample was evaluated with regard to the items shown in Table 3 by a sensory evaluation method of comparing a sample with a control product. The evaluation was performed by a panel of 5 trained experts. The sample was evaluated with the points in the range of −3 to +3, with setting the control product at 0 point. The control product was not provided with a flavor improving agent (provided with ethanol).

| <Method of sensory evaluation> | |
| --- | --- |
| +3 | Significantly improved |
| +2 | Improved |
| +1 | Slightly improved |
| 0 | No change |
| −1 | Slightly deteriorated |
| −2 | Deteriorated |
| −3 | Significantly deteriorated |

The results of the evaluation are shown in Table 3. The numerals in the table are the averages of the 5 experts.

Example 10

A sugar-free sweetener solution containing a flavor improving agent was prepared in the same manner as in Example 9 except that the flavor improving agent in Example 3 was used instead of the flavor improving agent in Example 2. Sensory evaluation of the solution was carried out in the same method as in Example 9.

The results of the evaluation are shown in Table 3. The numerals in the table are the averages of the 5 experts.

Comparative Example 4

1 g of water was added to 300 mg of commercially available αG hesperidin (produced by Toyo Sugar Refining Co., Ltd.) to prepare a flavor improving agent. 10 mg of the flavor improving agent and 60 mg of ethanol were added to 300 g of an aqueous solution of the sugar-free sweetener in Example 9 to prepare a sugar-free sweetener solution sample containing 0.001% by weight of αG hesperidin and 0.02% by weight of ethanol. Sensory evaluation of the sample was carried out in the same method as in Example 9.

The results of the evaluation are shown in Table 3. The numerals in the table are the averages of the 5 experts.

Comparative Example 5

1 g of water was added to 900 mg of commercially available potassium alum (produced by Nacalai Tesque, Inc.) to prepare a flavor improving agent. 10 mg of the flavor improving agent and 60 mg of ethanol were added to 300 g of an aqueous solution of the sugar-free sweetener in Example 9 to prepare a sugar-free sweetener solution sample containing 0.003% by weight of potassium alum and 0.02% by weight of ethanol. Sensory evaluation of the sample was carried out in the same method as in Example 9.

The results of the evaluation are shown in Table 3. The numerals in the table are the averages of the 5 experts.

TABLE 3

| Sensory evaluation of the flavor improving agents for the sugar-free sweetener | | | | |
| --- | --- | --- | --- | --- |
| | Example 9 | Example 10 | Comparative example 4 | Comparative example 5 |
| Improvement of unpleasant aftertaste | 2.2 | 2.0 | 1.3 | 0.7 |
| Improvement of astringency | 1.6 | 1.8 | 0.4 | −0.7 |
| Enhancement of the sense of volume | 1.7 | 2.1 | 0.3 | −0.2 |
| Improvement of attractiveness | 2.3 | 2.2 | 0.8 | −2.1 |

The flavor improving agents used in Example 9 and Example 10 exhibit an excellent effect of reducing unpleasant aftertaste and astringency. These flavor improving agents also exhibit an excellent effect of improving the sense of volume, which is insufficient in sugar-free sweeteners, and thus improve attractiveness of the sugar-free sweetener. By contrast, αG hesperidin and potassium alum exhibit a poor effect of reducing astringency or improving the sense of volume, and thus do not provide a sufficient improving effect.

Example 11

Preparation of a High-Intensity Sweetener Solution Containing a Flavor Improving Agent The high-intensity sweeteners shown in Table 4 were dissolved in ion exchanged water to prepare aqueous solutions of high-intensity sweeteners having the concentrations shown in Table 4. 0.02% by weight of the flavor improving agent in Example 3 was added to each aqueous solution to obtain a solution sample of the high-intensity sweetener. The content of 5-hydroxymethyl-2-furaldehyde bis(5-formylfurfuryl)acetal in each high-intensity sweetener was 0.00014% by weight.

TABLE 4

Concentration of each high-intensity sweetener

| | Sweetener | Concentration (%) |
|---|---|---|
| Aqueous solution A of high-intensity sweetener | Aspartame | 0.025 |
| Aqueous solution B of high-intensity sweetener | Suclarose | 0.0083 |
| Aqueous solution C of high-intensity sweetener | Acesulfame K | 0.025 |
| Aqueous solution D of high-intensity sweetener | Saccharine | 0.017 |
| Aqueous solution E of high-intensity sweetener | Stevia | 0.017 |

In the table, aspartame, suclarose, acesulfame K, saccharine and stevia are respectively produced by Ajinomoto Co., Inc., San-Ei Gen F.F.I., Inc., Takeda Pharmaceutical Company Limited, Daiwa Kasei K.K. and Toyo Sugar Refining Co., Ltd.

These samples were evaluated with regard to the items shown in Table 5 by a sensory evaluation method of comparing samples with a control product. The evaluation was performed by a panel of 5 trained experts. Sensory evaluation of each sample was carried out with the points in the range of −3 to +3, with setting the control product at 0 point, in the same manner as in Example 9. The control product was not provided with a flavor improving agent (provided with ethanol).

The results of the evaluation are shown in Table 5. The numerals in the table are the averages of the 5 experts.

TABLE 5

Sensory evaluation of the flavor improving agent for the high-intensity sweeteners

| | A | B | C | D | E |
|---|---|---|---|---|---|
| Improvement of unpleasant aftertaste | 2.6 | 1.8 | 2.2 | 1.8 | 2.4 |
| Improvement of astringency | 1.6 | 1.6 | 1.8 | 1.5 | 1.5 |
| Enhancement of the sense of volume | 1.8 | 1.5 | 1.6 | 2.2 | 1.8 |
| Improvement of attractiveness | 2.6 | 2.0 | 2.2 | 2.2 | 2.0 |

The flavor improving agent used in Example 11 exhibits an excellent effect of reducing unpleasant aftertaste and astringency for all the high-intensity sweeteners. The flavor improving agent also exhibits an excellent effect of improving the sense of volume, which is insufficient in high-intensity sweeteners, and thus improves attractiveness of the high-intensity sweeteners. It is understood that the flavor improving agent used in Example 11 is an excellent flavor improving agent.

Example 12

Preparation of a Sugar Alcohol Solution Containing a Flavor Improving Agent

The sweeteners shown in Table 6 were dissolved in ion exchanged water to prepare aqueous solutions of sugar alcohols having the concentrations shown in Table 6. 0.02% by weight of the flavor improving agent in Example 3 was added to each aqueous solution to obtain a solution sample of the sugar alcohol. The content of 5-hydroxymethyl-2-furaldehyde bis(5-formylfurfuryl)acetal in each sugar alcohol solution was 0.00014% by weight.

TABLE 6

Concentration of each sugar alcohol solution

| | Sweetener | Concentration (%) |
|---|---|---|
| Aqueous solution F of sugar alcohol | Reduced palatinose | 10.0 |
| Aqueous solution G of sugar alcohol | Sorbitol | 8.3 |
| Aqueous solution H of sugar alcohol | Maltitol | 6.3 |
| Aqueous solution J of sugar alcohol | Xylitol | 5.0 |

In the table, reduced palatinose, sorbitol, maltitol and xylitol are respectively produced by Mitsui Sugar Co., Ltd., Nikken Kagaku Kabushiki Kaisha, Towa Chemical Industry Co., Ltd. and Danisco Japan Ltd.

These samples were evaluated with regard to the items shown in Table 7 by a sensory evaluation method of comparing a sample with a control product. The evaluation was performed by a panel of 5 trained experts. Sensory evaluation of each sample was carried out with the points in the range of −3 to +3, with setting the control product at 0 point, in the same manner as in Example 9. The control product was not provided with a flavor improving agent (provided with ethanol).

The results of the evaluation are shown in Table 7. The numerals in the table are the averages of the 5 experts.

TABLE 7

Sensory evaluation of the flavor improving agent for the sugar alcohols

| | F | G | H | J |
|---|---|---|---|---|
| Improvement of unpleasant aftertaste | 2.0 | 1.8 | 1.8 | 2.2 |
| Improvement of astringency | 1.5 | 1.9 | 1.9 | 1.8 |
| Enhancement of the sense of volume | 1.5 | 2.2 | 1.9 | 2.1 |
| Improvement of attractiveness | 2.2 | 2.2 | 1.8 | 2.3 |

The flavor improving agent used in Example 12 exhibits an excellent effect of reducing unpleasant aftertaste and astringency for all the sugar alcohols. The flavor improving agent also exhibits an excellent effect of improving the sense of volume, which is insufficient in sugar alcohols, and thus improves attractiveness of the sugar alcohols. It is understood that the flavor improving agent used in Example 12 is an excellent flavor improving agent.

Example 13

Production of a Sugar-Free Candy Containing a Flavor Improving Agent 150 g of saccharified reduced starch and 150 g of water were added to 400 g of palatinit, and these substances were completely dissolved while being heated. The resultant substance was heated up to 170° C. and then cooled down to 140° C. Next, 0.35 g of aspartame and 0.11 g of the flavor improving agent in Example 4 (0.02% by weight) were added thereto, and the resultant substance was flown into a mold to be molded. Thus, a sugar-free candy was obtained. The content of 5-hydroxymethyl-2-furaldehyde bis(5-formylfurfuryl)acetal in this sugar-free candy was 0.00047% by weight.

This sugar-free candy was evaluated with regard to the items shown in Table 8 by a sensory evaluation method of comparing a sample with a control product. The evaluation was performed by a panel of 5 trained experts. Sensory evaluation of the sugar-free candy was carried out with the points in the range of −3 to +3, with setting the control product at 0 point, in the same manner as in Example 9. The control product was not provided with a flavor improving agent.

The results of the evaluation are shown in Table 8. The numerals in the table are the averages of the 5 experts.

Example 14

Production of a Sugar-Free Candy Containing a Flavor Improving Agent

A sugar-free candy containing a flavor improving agent was obtained in the same manner as in Example 13 except that the flavor improving agent in Example 6 (the content of 5-hydroxymethyl-2-furaldehyde bis(5-formylfurfuryl)acetal: 1.9% by weight) was used instead of the flavor improving agent in Example 4. Sensory evaluation of the sample was carried out in the same method as in Example 13.

The results of the evaluation are shown in Table 8. The numerals in the table are the averages of the 5 experts.

Comparative Example 6

Production of a Sugar-Free Candy Containing a Flavor Improving Agent

A sugar-free candy containing a flavor improving agent was obtained in the same manner as in Example 13 except that the flavor improving agent in Comparative example 1 was used instead of the flavor improving agent in Example 4. Sensory evaluation of the sample was carried out in the same method as in Example 13.

The results of the evaluation are shown in Table 8. The numerals in the table are the averages of the 5 experts.

Comparative Example 7

Production of a Sugar-Free Candy Containing a Flavor Improving Agent

A sugar-free candy containing a flavor improving agent was obtained in the same manner as in Example 13 except that the flavor improving agent in Comparative example 2 was used instead of the flavor improving agent in Example 4. Sensory evaluation of the sample was carried out in the same method as in Example 13.

The results of the evaluation are shown in Table 8. The numerals in the table are the averages of the 5 experts.

Comparative Example 8

Production of a Sugar-Free Candy Containing a Flavor Improving Agent

A sugar-free candy containing a flavor improving agent was obtained in the same manner as in Example 13 except that the flavor improving agent in Comparative example 3 was used instead of the flavor improving agent in Example 4. Sensory evaluation of the sample was carried out in the same method as in Example 13.

The results of the evaluation are shown in Table 8. The numerals in the table are the averages of the 5 experts.

The flavor improving agents used in Example 13 and Example 14 provide the sense of volume and the sense of roastedness, and especially strong sense of naturalness, to the sugar-free candy and thus improve attractiveness thereof. By contrast, the flavor improving agent used in Comparative example 6 does not exhibit a sufficient effect. The flavor improving agents used in Comparative examples 7 and 8 add various other tastes, and thus do not provide a sufficient improving effect. From the above, it is understood that the flavor improving agents used in Examples 13 and 14 are excellent flavor improving agents.

Example 15

Preparation of a Diet Cola Drink Containing a Flavor Improving Agent 30 mg of the flavor improving agent in Example 2 was added to 300 g of a commercially available diet cola drink to obtain a diet cola drink containing 0.01% by weight of the flavor improving agent. The content of 5-hydroxymethyl-2-furaldehyde bis(5-formylfurfuryl)acetal in this diet cola drink was 0.00007% by weight.

This diet cola drink was evaluated with regard to the items shown in Table 9 by a sensory evaluation method of comparing a sample with a control product. The evaluation was performed by a panel of 5 trained experts. Sensory evaluation of the diet cola drink was carried out with the points in the range of −3 to +3, with setting the control product at 0 point, in the same manner as in Example 9. The control product was not provided with a flavor improving agent (provided with ethanol).

The results of the evaluation are shown in Table 9. The numerals in the table are the averages of the 5 experts.

Example 16

Preparation of a Diet Cola Drink Containing a Flavor Improving Agent

A diet cola drink containing a flavor improving agent was obtained in the same manner as in Example 15 except that the flavor improving agent in Example 3 was used instead of the flavor improving agent in Example 2. Sensory evaluation of the drink was carried out in the same method as in Example 15.

The results of the evaluation are shown in Table 9. The numerals in the table are the averages of the 5 experts.

Example 17

Preparation of a Diet Cola Drink Containing a Flavor Improving Agent

A diet cola drink containing a flavor improving agent was obtained in the same manner as in Example 15 except that the

TABLE 8

Sensory evaluation of the flavor improving agents for the sugar-free candy

| | Example 13 | Example 14 | Comparative example 6 | Comparative example 7 | Comparative example 8 |
|---|---|---|---|---|---|
| Enhancement of the sense of volume | 2.4 | 2.5 | 1.2 | 0.3 | 0.2 |
| Enhancement of the sense of naturalness | 2.6 | 2.5 | 0.5 | 0.1 | 0.0 |
| Enhancement of the sense of roastedness | 2.0 | 2.0 | 0.8 | 0.0 | 0.0 |
| Improvement of attractiveness | 2.4 | 2.3 | 0.7 | 0.2 | 0.1 | flavor improving agent in Example 7 was used instead of the flavor improving agent in Example 2. The content of 5-hydroxymethyl-2-furaldehyde bis(5-formylfurfuryl)acetal in this diet cola drink was 0.00001% by weight. Sensory evaluation of the drink was carried out in the same method as in Example 15.

The results of the evaluation are shown in Table 9. The numerals in the table are the averages of the 5 experts.

TABLE 9

Sensory evaluation of the flavor improving agents for the diet cola drink

|  | Example 15 | Example 16 | Example 17 |
|---|---|---|---|
| Improvement of unpleasant aftertaste | 2.2 | 2.4 | 1.8 |
| Enhancement of the sense of refreshment | 1.8 | 2.0 | 1.7 |
| Enhancement of the sense of volume | 2.0 | 2.0 | 1.6 |
| Improvement of attractiveness | 2.6 | 2.4 | 1.7 |

The flavor improving agents used in Example 15, Example 16 and Example 17 provide the sense of refreshment and the sense of volume to, and also improve the sharpness of the sweet aftertaste of, the diet cola drink, and thus improve attractiveness thereof.

Example 18

Preparation of a Coffee Drink Containing a Flavor Improving Agent 60 mg of the flavor improving agent in Example 2 was added to 300 g of commercially available canned coffee to obtain a coffee drink containing 0.02% by weight of the flavor improving agent. The content of 5-hydroxymethyl-2-furaldehyde bis(5-formylfurfuryl)acetal in this coffee drink was 0.00014% by weight.

This coffee drink was evaluated with regard to the items shown in Table 10 by a sensory evaluation method of comparing a sample with a control product. The evaluation was performed by a panel of 5 trained experts. Sensory evaluation of the coffee drink was carried out with the points in the range of −3 to +3, with setting the control product at 0 point, in the same manner as in Example 9. The control product was not provided with a flavor improving agent (provided with ethanol).

The results of the evaluation are shown in Table 10. The numerals in the table are the averages of the 5 experts.

Example 19

Preparation of a Coffee Drink Containing a Flavor Improving Agent

A coffee drink containing a flavor improving agent was obtained in the same manner as in Example 18 except that the flavor improving agent in Example 3 was used instead of the flavor improving agent in Example 2. Sensory evaluation of the drink was carried out in the same method as in Example 18.

The results of the evaluation are shown in Table 10. The numerals in the table are the averages of the 5 experts.

Comparative Example 9

10 g of ethanol was added to 30 mg of commercially available naringin (produced by Towa Sangyo Kabushiki Kaisha) to prepare a flavor improving agent. In a similar manner to that in Example 18, 60 mg of the flavor improving agent was added to 300 g of the sample canned coffee to prepare a coffee drink containing 0.00006% by weight of naringin and 0.02% by weight of ethanol. Sensory evaluation of the coffee drink was carried out in the same method as in Example 18.

The results of the evaluation are shown in Table 10. The numerals in the table are the averages of the 5 experts.

Comparative Example 10

10 g of ethanol was added to 15 mg of commercially available quassia extract (produced by Towa Sangyo Kabushiki Kaisha) to prepare a flavor improving agent. In a similar manner to that in Example 18, 60 mg of the flavor improving agent was added to 300 g of the sample canned coffee to prepare a coffee drink containing 0.00003% by weight of quassia extract and 0.02% by weight of ethanol. Sensory evaluation of the coffee drink was carried out in the same method as in Example 18.

The results of the evaluation are shown in Table 10. The numerals in the table are the averages of the 5 experts.

Comparative Example 11

1.8 g of diheterolevulosan II which was prepared as described in reference example 1 of Japanese Laid-Open Patent Publication No. 11-103814 and 60 mg of ethanol were added to 300 g of the sample canned coffee to prepare a coffee drink containing 0.6% by weight of diheterolevulosan II and 0.02% by weight of ethanol. Sensory evaluation of the coffee drink was carried out in the same method as in Example 18.

The results of the evaluation are shown in Table 10. The numerals in the table are the averages of the 5 experts.

Comparative Example 12

3.8 mg of diheterolevulosan II which was prepared as described in reference example 1 of Japanese Laid-Open Patent Publication No. 11-103814 and 60 mg of ethanol were added to 300 g of the sample canned coffee to prepare a coffee drink containing 0.00127% by weight of diheterolevulosan II and 0.02% by weight of ethanol. Sensory evaluation of the coffee drink was carried out in the same method as in Example 18.

The results of the evaluation are shown in Table 10. The numerals in the table are the averages of the 5 experts.

TABLE 10

Sensory evaluation of the flavor improving agents for the coffee drink

|  | Example 18 | Example 19 | Comparative example 9 | Comparative example 10 | Comparative example 11 | Comparative example 12 |
|---|---|---|---|---|---|---|
| Improvement of the sharpness of bitter taste | 1.6 | 1.8 | 0.9 | −0.8 | 0.8 | 0.2 |
| Reduction of medicine-like unnatural bitter taste | 1.6 | 1.5 | −1.4 | −2.4 | −1.0 | 0.0 |

TABLE 10-continued

Sensory evaluation of the flavor improving agents for the coffee drink

|  | Example 18 | Example 19 | Comparative example 9 | Comparative example 10 | Comparative example 11 | Comparative example 12 |
|---|---|---|---|---|---|---|
| Enhancement of the sense of roastedness | 2.4 | 2.8 | 1.4 | 1.4 | 1.3 | 0.2 |
| Enhancement of the sense of volume | 2.0 | 2.1 | 0.8 | 0.6 | 0.9 | 0.2 |
| Improvement of attractiveness | 2.4 | 2.8 | 0.5 | −2.4 | 0.6 | 0.2 |

The flavor improving agents used in Example 18 and Example 19 provide sharp and high-quality bitterness, sense of roastedness and sense of volume to the coffee drink and thus improve attractiveness thereof. By contrast, naringin, quassia extract, and diheterolevulosan II have medicine-like unnatural bitterness and are poor in attractiveness. In Comparative example 12 in which diheterolevulosan II was added in an amount about 10 times as much as that of the 5-hydroxymethyl-2-furaldehyde bis(5-formylfurfuryl)acetal used in Example 18, no change was sensed in the flavor. From these, it is understood that the flavor improving agents used in Examples 18 and 19 are excellent flavor improving agents.

Example 20

Preparation of Vanilla Ice Cream Containing a Flavor Improving Agent 10 mg of the flavor improving agent in Example 4 was added to 100 g of commercially available vanilla ice cream to obtain vanilla ice cream containing 0.01% by weight of the flavor improving agent. The content of 5-hydroxymethyl-2-furaldehyde bis(5-formylfurfuryl)acetal in this vanilla ice cream was 0.00023% by weight.

This ice cream was evaluated with regard to the items shown in Table 11 by a sensory evaluation method of comparing a sample with a control product. The evaluation was performed by a panel of 5 trained experts. Sensory evaluation of the ice cream was carried out with the points in the range of −3 to +3, with setting the control product at 0 point, in the same manner as in Example 9. The control product was not provided with a flavor improving agent.

The results of the evaluation are shown in Table 11. The numerals in the table are the averages of the 5 experts.

TABLE 11

Sensory evaluation of the flavor improving agent for the vanilla ice cream

|  | Example 20 |
|---|---|
| Enhancement of the sense of volume | 2.0 |
| Enhancement of the sense of vanilla | 1.8 |
| Improvement of attractiveness | 1.8 |

The flavor improving agent used in Example 20 provides the sense of vanilla and the sense of volume to the vanilla ice cream and thus improves attractiveness thereof.

Example 21

Preparation of Chocolate Containing a Flavor Improving Agent 100 g of commercially available couverture chocolate which was placed in a vessel was put into water of 50° C. to be dissolved. The flavor improving agent in Example 4 was added thereto such that 30 mg of the flavor improving agent would be mixed, and stirred. The temperature was once lowered to about 28° C. and then raised to about 30° C. to perform tempering. Next, the resultant substance was flown into a mold to be molded and cooled to obtain a chocolate sample containing 0.03% by weight of the flavor improving agent. The content of 5-hydroxymethyl-2-furaldehyde bis(5-formylfurfuryl)acetal in this chocolate was 0.00070% by weight.

This chocolate sample was evaluated with regard to the items shown in Table 12 by a sensory evaluation method of comparing a sample with a control product. The evaluation was performed by a panel of 5 trained experts. Sensory evaluation of the sample was carried out with the points in the range of −3 to +3, with setting the control product at 0 point. The control product was not provided with a flavor improving agent.

The results of the evaluation are shown in Table 12. The numerals in the table are the averages of the 5 experts.

Example 22

Preparation of Chocolate Containing a Flavor Improving Agent

The same operation as that in Example 21 was performed except that the flavor improving agent in Example 5 was added such that 150 mg thereof would be contained instead of the flavor improving agent in Example 4. Thus, a chocolate sample containing 0.15% by weight of the flavor improving agent was prepared. The content of 5-hydroxymethyl-2-furaldehyde bis(5-formylfurfuryl)acetal in this chocolate was 0.0069% by weight. Sensory evaluation of the sample was carried out in the same method as in Example 21.

The results of the evaluation are shown in Table 12. The numerals in the table are the averages of the 5 experts.

TABLE 12

Sensory evaluation of the flavor improving agents for the chocolate

|  | Example 21 | Example 22 |
|---|---|---|
| Improvement of the sharpness of sweet taste | 2.6 | 2.6 |
| Enhancement of the sense of volume | 2.2 | 2.0 |
| Enhancement of the sense of cacao | 2.2 | 2.6 |
| Improvement of attractiveness | 1.8 | 1.6 |

The flavor improving agents used in Example 21 and Example 22 provide the sense of volume and the sense of cacao to, and also improve the sharpness of sweet taste of the chocolate sample. In addition, in Example 22, strong bitterness was sensed.

Example 23

Preparation of Chocolate Containing an Aroma Material Composition 100 g of commercially available couverture chocolate which was placed in a vessel was put into water of 50° C. to be dissolved. The aroma material composition in Example 8 was added thereto such that 100 mg of the aroma material composition agent would be mixed, and stirred. The temperature was once lowered to about 28° C. and then raised to about 30° C. to obtain a chocolate sample containing 0.1% by weight of the aroma material composition. The content of 5-hydroxymethyl-2-furaldehyde bis(5-formylfurfuryl)acetal in this chocolate was 0.00070% by weight. Sensory evaluation of the sample was carried out in the same method as in Example 21.

The results of the evaluation are shown in Table 13. The numerals in the table are the averages of the 5 experts.

TABLE 13

Sensory evaluation of the aroma material composition for the chocolate

|  | Example 23 |
|---|---|
| Improvement of the sharpness of sweet taste | 2.5 |
| Enhancement of the sense of volume | 2.5 |
| Enhancement of the sense of cacao | 2.8 |
| Improvement of attractiveness | 2.2 |
| Improvement of the diffusion of aroma | 2.5 |

The aroma material composition in Example 23 provided the sense of volume and the sense of cacao to the chocolate sample, improved the diffusion of aroma, and the sharpness of sweet taste thereof.

Example 24

Preparation of a Noodle Soup Containing a Flavor Improving Agent 60 mg of the flavor improving agent in Example 3 was added to 300 mL of a solution obtained by diluting a commercially available double concentrated noodle soup 4-fold with water, to obtain a noodle soup sample containing 0.02% by weight of the flavor improving agent. The content of 5-hydroxymethyl-2-furaldehyde bis(5-formylfurfuryl)acetal in this noodle soup was 0.00014% by weight.

This noodle soup sample was evaluated with regard to the items shown in Table 14 by a sensory evaluation method of comparing a sample with a control product. The evaluation was performed by a panel of 5 trained experts. Sensory evaluation of the sample was carried out with the points in the range of −3 to +3, with setting the control product at 0 point, in the same manner as in Example 9. The control product was not provided with a flavor improving agent (provided with ethanol).

The results of the evaluation are shown in Table 14. The numerals in the table are the averages of the 5 experts.

Example 25

Preparation of a Noodle Soup Containing a Flavor Improving Agent

A noodle soup containing a flavor improving agent was prepared in the same manner as in Example 24 except that the flavor improving agent in Example 7 was used instead of the flavor improving agent in Example 3. The content of 5-hydroxymethyl-2-furaldehyde bis(5-formylfurfuryl)acetal in this noodle soup was 0.00002% by weight. Sensory evaluation of the sample was carried out in the same method as in Example 24.

The results of the evaluation are shown in Table 14. The numerals in the table are the averages of the 5 experts.

TABLE 14

Sensory evaluation of the flavor improving agents for the noodle soup

|  | Example 24 | Example 25 |
|---|---|---|
| Enhancement of thickness in taste | 2.2 | 1.8 |
| Enhancement of depth in taste | 2.0 | 1.6 |
| Improvement of attractiveness | 1.8 | 1.6 |

The flavor improving agents used in Examples 24 and 25 provide thickness and depth to the noodle soup and improve attractiveness thereof.

Reference Example 100 mg of 5-hydroxymethyl-2-furaldehyde bis(5-formylfurfuryl)acetal obtained in Example 1 was dissolved in 1 mL of ethanol, and 100 mL of water was added to produce 0.1% by weight of a 1 wt. % ethanol solution. This solution was diluted 10-fold with water repeatedly to prepare samples for evaluation. In consideration of the taste of ethanol itself, a 1 wt. % ethanol solution was prepared and diluted 10-fold with water repeatedly to prepare blanks respectively corresponding to the samples for evaluation. The evaluation was performed by a panel of 9 experts. The sensory evaluation test was performed from a sample/blank having a lower concentration. In the order of blanks to samples, the experts held 200 mg of each sample/blank in the mouth and evaluated the difference in taste.

As a result of the test, the bitterness threshold was 1 ppm. When converted to the molar concentration, this threshold is about $10^{-3}$ mM and is about the same as that of quinine hydrochloride, which is a representative of bitter substances.

Substantially the same test was performed on the compounds of formulas (2) and (3). Even at 0.1% by weight, which is the maximum concentration, these compounds did not provide bitterness.

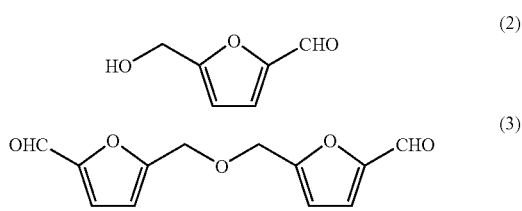

The same type of test as that in Example 9 was performed on agents which were prepared as described in Example 2 except that the compounds of formulas (2) and (3) were used instead of 5-hydroxymethyl-2-furaldehyde bis(5-formylfurfuryl)acetal and also agents which were prepared with 100 times the amount of the compounds of formulas (2) and (3). None of the agents exhibited any flavor improving effect and provided various unpleasant tastes including astringency.

As described above, the bitterness threshold of the acetal compound of the present invention is 1 ppm (0.0001% by weight), but it should be understood that the flavor improving effect is provided even at a level at which bitterness is not sensed.

INDUSTRIAL APPLICABILITY

A flavor improving agent according to the present invention, when being incorporated into foods/drinks, pharmaceutical products, oral care products and the like, sufficiently enhances or alleviates the flavor sensed in oral cavity; for example, the flavor improving agent enhances and improves the thickness in taste or the like to provide depth and profoundness to the taste, and also improves the sense of volume or the sharpness of aftertaste. According to the present invention, foods/drinks, pharmaceutical products and oral care products having a good taste which can fulfill the recent high-level demand for taste can be provided.

The invention claimed is:

1. 5-hydroxymethyl-2-furaldehyde bis(5-formylfurfuryl)acetal.

2. A composition comprising at least 0.1% by weight of 5-hydroxymethyl-2-furaldehyde bis(5-formylfurfuryl)acetal.

3. A composition comprising at least 0.7% by weight of 5-hydroxymethyl-2-furaldehyde bis(5-formylfurfuryl)acetal.

4. A flavor improving agent comprising 5-hydroxymethyl-2-furaldehyde bis(5-formylfurfuryl)acetal as an effective ingredient.

5. The flavor improving agent according to claim 4, further comprising an aroma material.

6. The flavor improving agent according to claim 4, wherein the content of 5-hydroxymethyl-2-furaldehyde bis(5-formylfurfuryl)acetal is at least 0.1% by weight.

7. The flavor improving agent according to claim 4, wherein the content of 5-hydroxymethyl-2-furaldehyde bis(5-formylfurfuryl)acetal is at least 0.7% by weight.

8. An aroma material composition comprising 5-hydroxymethyl-2-furaldehyde bis(5-formylfurfuryl)acetal and an aroma material.

9. The aroma material composition according to claim 8, wherein the content of 5-hydroxymethyl-2-furaldehyde bis(5-formylfurfuryl)acetal is 0.000001 to 50% by weight.

10. The aroma material composition according to claim 8, wherein the content of 5-hydroxymethyl-2-furaldehyde bis(5-formylfurfuryl)acetal is 0.00001 to 10% by weight.

11. A food/drink comprising a flavor improving agent comprising i) the compound of claim 1 as an effective ingredient, or ii) an aroma material composition comprising the compound of claim 1 and an aroma material.

12. The food/drink according to claim 11, wherein the content of 5-hydroxymethyl-2-furaldehyde bis(5-formylfurfuryl)acetal is 1 ppb to 1000 ppm.

13. A pharmaceutical product comprising a flavor improving agent comprising i) the compound of claim 1 as an effective ingredient, or ii) an aroma material composition comprising the compound of claim 1 and an aroma material.

14. The pharmaceutical product according to claim 13, wherein the content of 5-hydroxymethyl-2-furaldehyde bis(5-formylfurfuryl)acetal is 1 ppb to 1000 ppm.

15. An oral care product comprising a flavor improving agent comprising i) the compound of claim 1 as an effective ingredient, or ii) an aroma material composition comprising the compound of claim 1 and an aroma material.

16. The oral care product according to claim 15, wherein the content of 5-hydroxymethyl-2-furaldehyde bis(5-formylfurfuryl)acetal is 1 ppb to 1000 ppm.

* * * * *